United States Patent
Stjernström

(10) Patent No.: US 7,323,345 B1
(45) Date of Patent: Jan. 29, 2008

(54) LIQUID MICROVOLUME HANDLING SYSTEM

(75) Inventor: Mårten Stjernström, Stockholm (SE)

(73) Assignee: Norada Holding AB, Stockholm (SE)

( * ) Notice: Subject to any disclaimer, the term of this patent is extended or adjusted under 35 U.S.C. 154(b) by 0 days.

(21) Appl. No.: 09/830,795

(22) PCT Filed: Oct. 29, 1999

(86) PCT No.: PCT/SE99/01958

§ 371 (c)(1),
(2), (4) Date: Apr. 30, 2001

(87) PCT Pub. No.: WO00/25921

PCT Pub. Date: May 11, 2000

(30) Foreign Application Priority Data

Oct. 30, 1998 (SE) .................................. 9803734

(51) Int. Cl.
*G01N 1/10* (2006.01)
(52) U.S. Cl. ..................... 436/180; 436/174; 436/176; 436/179; 422/99; 422/100; 422/102
(58) Field of Classification Search ............... 422/68.1, 422/79, 100, 102, 103; 436/174, 179, 180, 436/176
See application file for complete search history.

(56) References Cited

U.S. PATENT DOCUMENTS

| | | | | |
|---|---|---|---|---|
| 4,507,463 A | * | 3/1985 | Orban ......................... | 528/279 |
| 4,659,677 A | | 4/1987 | Glover et al. | |
| 5,171,989 A | * | 12/1992 | Williams et al. ............. | 250/288 |
| 5,198,353 A | * | 3/1993 | Hawkins et al. ............. | 435/188 |
| 5,593,838 A | | 1/1997 | Zanzucchi et al. | |
| 5,783,148 A | | 7/1998 | Cottingham et al. | |
| 5,785,926 A | | 7/1998 | Seubert et al. | |
| 5,846,396 A | * | 12/1998 | Zanzucchi et al. .......... | 204/601 |
| 5,863,801 A | * | 1/1999 | Southgate et al. .......... | 422/101 |
| 5,879,632 A | * | 3/1999 | Demers ....................... | 422/100 |
| 6,033,544 A | * | 3/2000 | Demers et al. ............. | 204/450 |
| 6,143,247 A | * | 11/2000 | Sheppard, Jr. et al. ........ | 422/63 |
| 6,143,248 A | * | 11/2000 | Kellogg et al. ............... | 422/72 |
| 6,319,469 B1 | * | 11/2001 | Mian et al. .................... | 422/64 |
| 6,416,642 B1 | * | 7/2002 | Alajoki et al. .............. | 204/451 |
| 6,451,188 B1 | * | 9/2002 | Sundberg et al. .......... | 204/453 |
| 6,488,895 B1 | * | 12/2002 | Kennedy .................... | 422/100 |

(Continued)

FOREIGN PATENT DOCUMENTS

EP          88307946.9          8/1988

(Continued)

*Primary Examiner*—Jill Warden
*Assistant Examiner*—Dwayne K Handy
(74) *Attorney, Agent, or Firm*—Fulbright & Jaworski LLP

(57) ABSTRACT

The present invention relates to a microfluidic device comprising a microchannel (2, 4) providing for solvent contact between an open microarea (MA) carrying a microvolume (1) of a solvent and a reservoir (3) for the solvent, said reservoir (3) and said microchannel (2, 4) being adapted so that solvent evaporated from said microarea (MA) is continuously replaced by solvent from the reservoir (3) through said microchannel (2, 4). It further relates to method for replacing solvents evaporating from a microvolume (1) of solvent placed in an open microarea (MA) of a microfluidic device, wherein replacement is continuously taking place via a microchannel (2, 4) that transports solvent to the microarea (MA) from a solvent reservoir (vessel) (3). The device and method are suitable for preventing the desiccation of samples.

8 Claims, 5 Drawing Sheets

U.S. PATENT DOCUMENTS 6,642,061 B2 * 11/2003 Ellson et al. ............... 436/180

FOREIGN PATENT DOCUMENTS

| WO | WO/98/33052 | 7/1998 |
|----|-------------|--------|
| WO | WO/99/44746 | 9/1999 |
| WO | WO/00/67907 | 11/2000 |
| WO | WO/00/67907 A3 | 11/2000 |

* cited by examiner

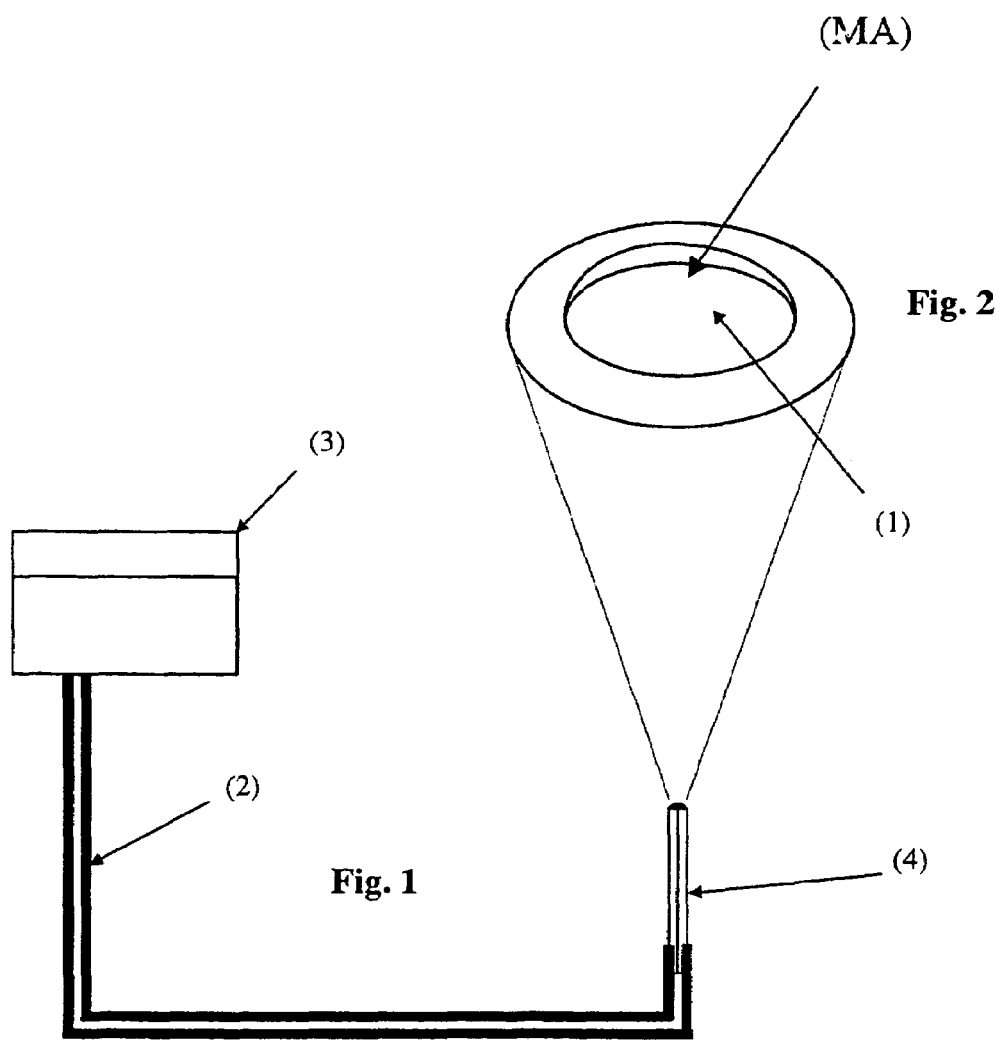

LIQUID MICROVOLUME HANDLING SYSTEM

TECHNICAL FIELD

The present invention relates to microfluidic devices comprising microchannels, and to methods for replacing solvent amounts that evaporate from open microareas carrying microvolumes of the solvent. The resent invention also relates to the use of the method for replacing solvent in a method for preventing the desiccation of samples. The microvolume of solvent may be in the form of a droplet (microdrop).

BACKGROUND ART

Microvolume handling systems have attracted a considerable interest in biochemical analysis, combinatorial chemistry and high throughput screening (HTS) applications. The miniaturised format is compatible in size with many interesting issues of bioanalytical work, such as single cell analysis, when material is available only in extremely limited amounts. Furthermore, by decreasing the volume, an enhanced efficiency in terms of a higher rate of mixing and/or chemical reaction can be expected in the sample container, since the effect of diffusion and thermal convection is more pronounced on a smaller scale.

In HTS applications, goals are currently set on screening more than $10^5$ compounds in a single assay. To manage such a tremendous number of samples with reasonable space, cost and time requirements, the miniaturised microtitre plate format has been developed. Based on micromachining of different materials, e.g., by anisotropically etching single crystalline silicon wafers, well-defined picoliter to nanoliter vials are readily fabricated (Jansson et al. (1992) J. Chromatography 626, 310-314; Beyer Hietpas et al. (1995) J. Liq. Chromatography 18, 3557-3576). Biomolecules such as DNA and proteins have been assayed in the microvial format utilising capillary electrophoresis (Jansson et al. supra; Beyer Hietpas et al., supra), bioluminescence (Crofcheck et al. (1997) Anal. Chem. 69, 4768-4772), electrochemical analysis (Clark et al. (1997) Anal. Chem. 69, 259-263; Clark et al. (1998) Anal. Chem. 70, 1119-1125) and mass spectrometry (Jespersen et al. (1994) J. Rapid Comm. in Mass Spectrom. 8, 581-584).

However, the rate of solvent evaporation is particularly pronounced for microvolumes, for instance small droplets, since the surface-to-volume ratio increases when the drop diameter decreases. The most common way for avoiding desiccation is by covering the containers with a material non-permeable for the underlying solvent. However, covers, either liquid or solid, inherently have the potential to introduce interfering compounds, or to alter equilibriums, that can seriously damage sensitive chemical systems. Furthermore, practical problems may arise from small droplets sticking to a solid cover.

An alternative is to diminish the solvent loss by controlling the environment in humidified chambers and by dispensing compensating solvent into the microvials via fine capillaries from above (Roeraade et al. (1996) Analytical Methods and Instrumentation. Special issue µTAS'96 (1996), pp. 34-38). However, this technique can be ineffective over prolonged time periods and is subject to many practical problems associated with the restricted accessibility to the vials through the environmental chamber. Furthermore, since the solvent compensating capillaries block the space in close proximity to the microvials, accessing or detecting the material becomes increasingly more complex as the assay becomes larger.

There is a need for microfluidic devices including a system for handling small volumetric amounts of liquid which avoids the above discussed drawbacks and allows for free access to the contained material, thus facilitating chemical manipulation of the liquid or the gaseous headspace environment and for monitoring of reaction products.

A device having the features of claim 1 and a method having the features of claim 6 fulfill this need.

BRIEF DESCRIPTION OF THE DRAWINGS

Examples of embodiments of the present invention are illustrated in the accompanying figures, where:

FIG. 1 is a schematic view of a first embodiment of a system in accordance with the present invention for containing small amounts of material in a droplet on top of the orifice of a microchannel;

FIG. 2 is an enlarged view of the top of the capillary in FIG. 1 illustrating a droplet;

DISCLOSURE OF THE INVENTION

Figure 3:
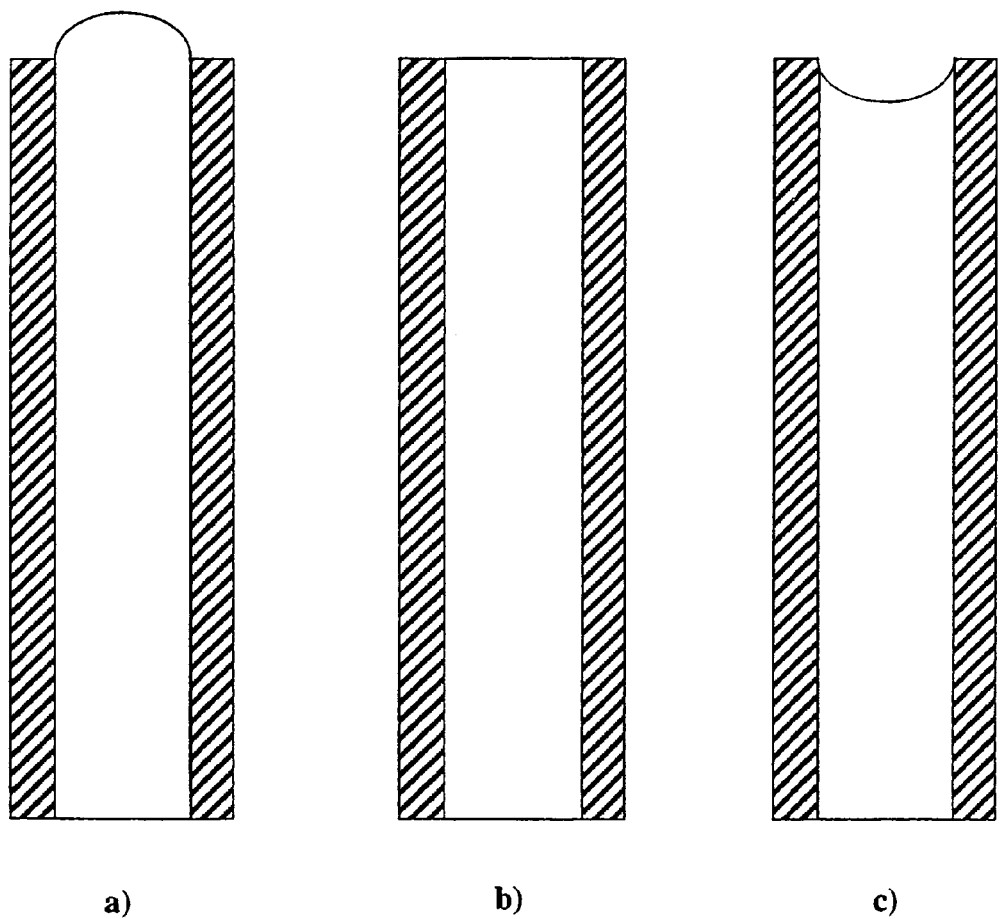
FIG. 3 illustrates the three different possible shapes of the liquid-gaseous interface.

The present invention provides a method for replacing solvent that is evaporating from a microvolume of solvent placed in an open microarea (MA) of a microfluidic device. The method has the characterising feature that replacement takes place continuously via a microchannel (2) that transports liquid to the microarea (MA) from a liquid reservoir (vessel). The method is particularly useful in the context of running reactions in the solvent present on the microarea (MA) in order to assay an analyte, for the synthesis of chemical compounds etc. The reactants used, including an analyte and/or various reagents, may be soluble in the microvolume or immobilised to a solid support in contact with the microvolume. The microarea (MA) may be the orifice region of the microchannel and the microvolume in the form of a microdrop (1), as shown in FIG. 2. By continuously replacing the evaporated solvent via a conduit (2) with solvent from a communicating vessel (3) the reactants present in the microvolume are prevented from being desiccated. The sample is focused in the microvolume as long as the evaporation rate of the solvent is higher than the sample diffusion rate. It should be noted that the solvent compensating principle is generally applicable to minute volumes, thus the liquid-gaseous interface may appear in any of the different shapes illustrated in FIGS. 3 a)-c). In the case of droplets shown FIG. 3 a), they can be formed by applying an overpressure to the solvent supplying tubing. This causes the droplet size to be determined by the diameter of the capillary orifice, the interfacial tension, the wettability of the capillary material and the magnitude of the applied overpressure (which needs to be in equilibrium with the interfacial pressure difference across the curved surface of the droplet). The microarea (MA) can be located either, as illustrated in FIG. 1, on top of a single capillary (4), or as shown in FIGS. 5-8, as an array of microareas carrying liquid in the form of drops (6) or liquid in the form of other physical microappearances (9) (e.g. surfaces of the type shown in FIGS. 3 b)-c)) formed on top of an array of fabricated holes (7) each supplied from a common solvent container (8). In the case of droplets, the overpressure needed can be created by any means of pressure generation, e.g. from a hydrostatic head, a micropump or a pressurised container.

The open geometry in this invention, with microareas carrying analyte- and/or reagent-containing solvent in direct contact with the surrounding gaseous phase, is favourable with respect to easy accessibility. For example, wet-chemical reactions can easily be performed with sample components contained in the surface layers, using reagents dispensed from external means directly to the microvolume of liquid placed in the microarea, for instance from ink-jet dispensers or fine pipettes. Furthermore, detection of analytes or reaction products can readily be made by using optical detectors, such as CCD-cameras. Moreover, the equilibrium between the solvent on the microarea and the surrounding gaseous phase could be exploited for passive sampling of air-born constituents over prolonged time periods, thus enabling subsequent environmental analysis.

The solvents contemplated are often aqueous, i.e. consists of water, possibly mixed with one or more water-miscible liquids, such as acetone, methanol, ethanol and isopropanol. This does not exclude the use of other solvents in the invention.

A second aspect of the invention relates to a microfluidic device comprising a microchannel providing for liquid contact between an open microarea carrying a microvolume of a solvent and a reservoir for the solvent, said reservoir and said microchannel being adapted so that solvent evaporated from said microarea is continuously replaced by solvent from the reservoir through said microchannel. When in use the microvolume of solvent typically contains an analyte and/or one or more reagents for assaying the analyte either directly or indirectly, for running synthesis of a compound etc. By the term "indirectly" is contemplated that a feature or an amount of a reaction product related to the analyte is assayed.

In order to avoid the risk of desiccation of the microareas over prolonged time periods, the supplying solvent vessel should contain a solvent volume one, two three or more orders of magnitude larger than the sum of all microvolumes communicating with the reservoir.

The term "microvolume" means a volume that typically is at most around 10 µl, such as $\leq 1$ µl. The lower end of the range extends down to the infinitesimal volume that is present in the gaseous-liquid interface of the microvolume of the solvent. Typically the microvolume is $\geq 10^{-15}$ (femtoliter). It will be understood, however, that the described principles may be applicable also to microvolumes being larger than 10 µl. By "microfluidic device" is meant a device that can handle microvolumes, for example a volume that is less than 1 µl, preferably between 1 and 10 nl, of reagents that may be introduced into the device.

A microarea may have different forms that vary from being an essentially flat form via cup-formed areas to being walls of open chambers, the important matter being that the area is able to carry the microvolume of liquid contemplated.

Microchannels typically have the ability to act as capillaries. Normally their size in the dimension (i.e. height, width or length) in which they are smallest is less than 2000 µm, such as $\leq 500$ µm. Typically this dimension is $\geq 1$ µm. A microchannel may be in form of a tube that may have a circular, a rectangular etc cross sectional area. They may also be "sheet"-like covering larger areas.

The reagents included in or in contact with the microvolume of solvent vary depending on the reaction to be run. The reagents include catalysts, for instance, an enzyme, compounds needed for the synthesis of nucleic acids, affinity reactants, etc. The term also includes biological systems, such as enzymatic systems and whole cells. Affinity reactants typically form non-covalent complexes and may be illustrated by biotin, streptavidin, protein A, antibodies, lectins, hormone receptors, nucleic acids, peptides and polypeptides. Typical assays are immunoassays, sequencing of nucleic acids and of peptides, hybridisation assays, detection of mutations, cell assays, etc.

Figure 4:
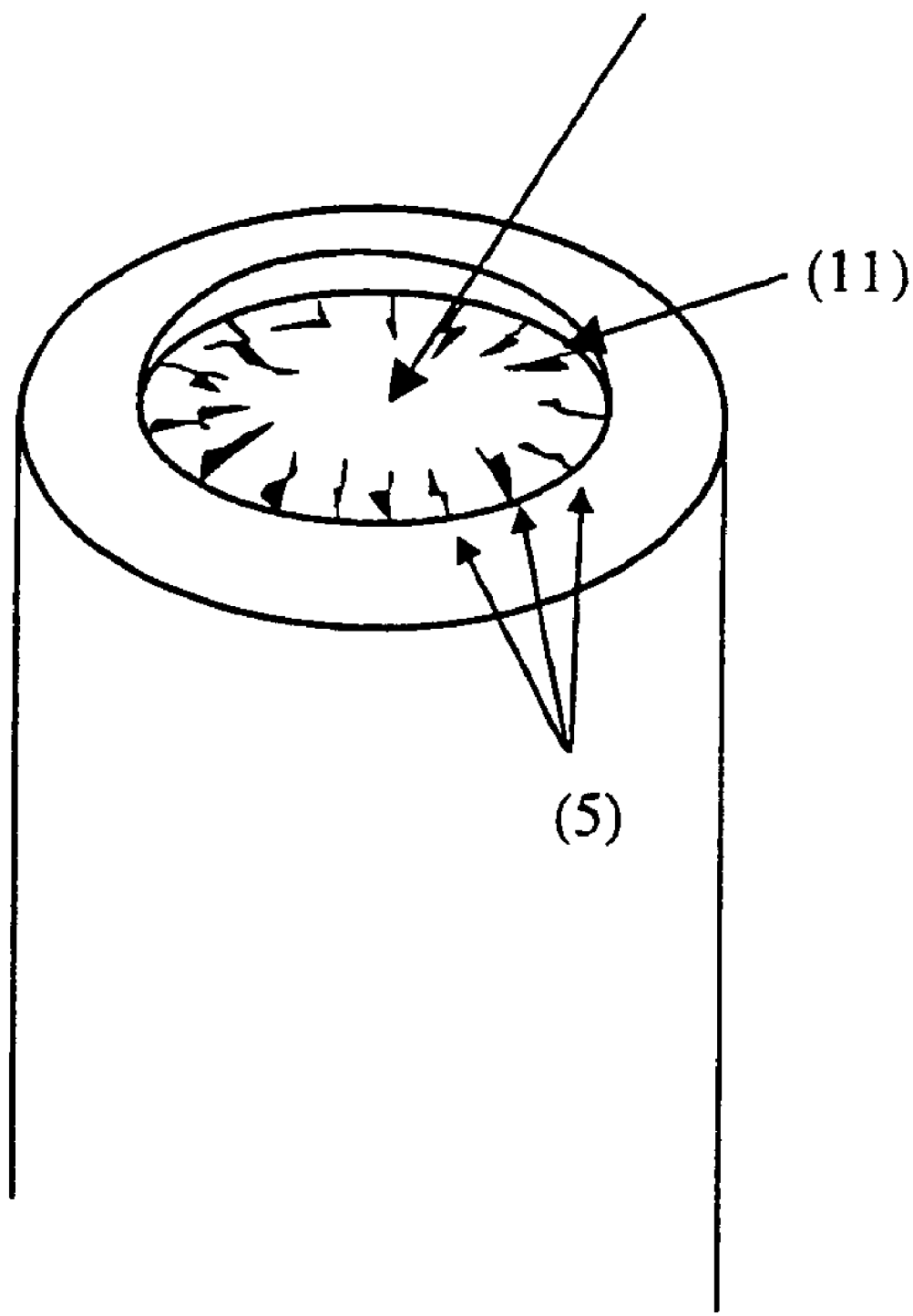
FIG. 4 illustrates a top of an embodiment of a microchannel in accordance with the present invention with a droplet and sample components immobilised on the microchannel rim.
Figure 5:
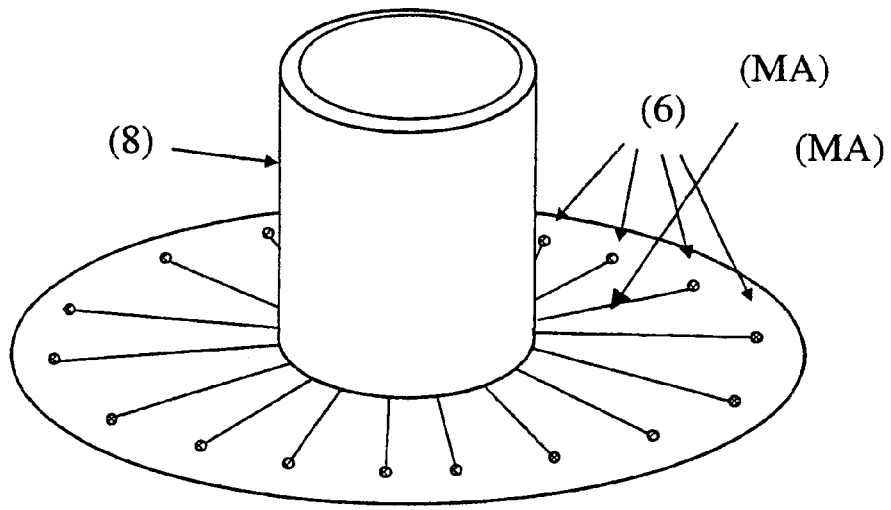
FIG. 5 illustrates a circular array of fabricated holes containing microdrops in accordance with other embodiment of the present invention.
Figure 6:
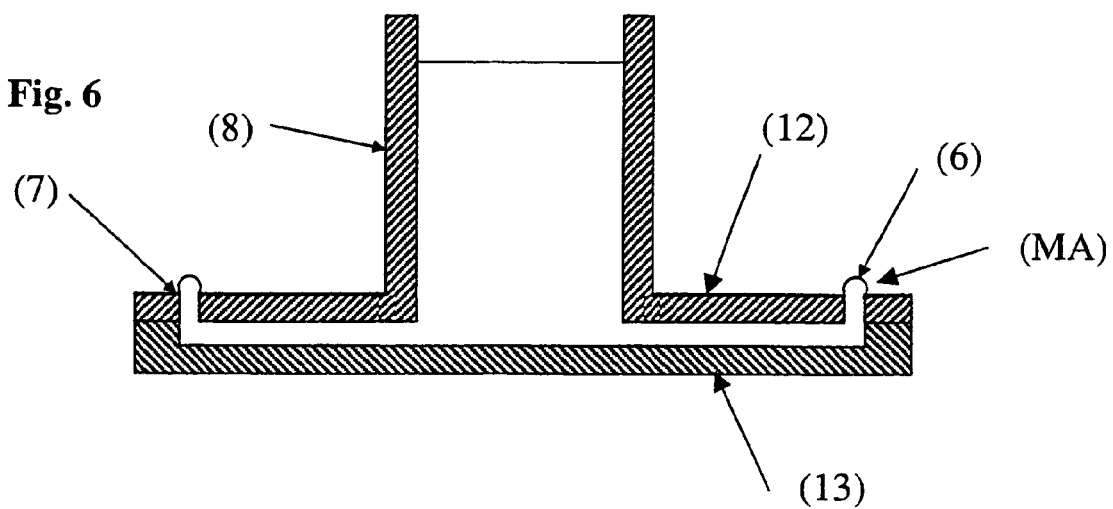
FIG. 6 is a sectional view of FIG. 3 illustrating a solvent container in accordance with an embodiment of the present invention.
Figure 7:
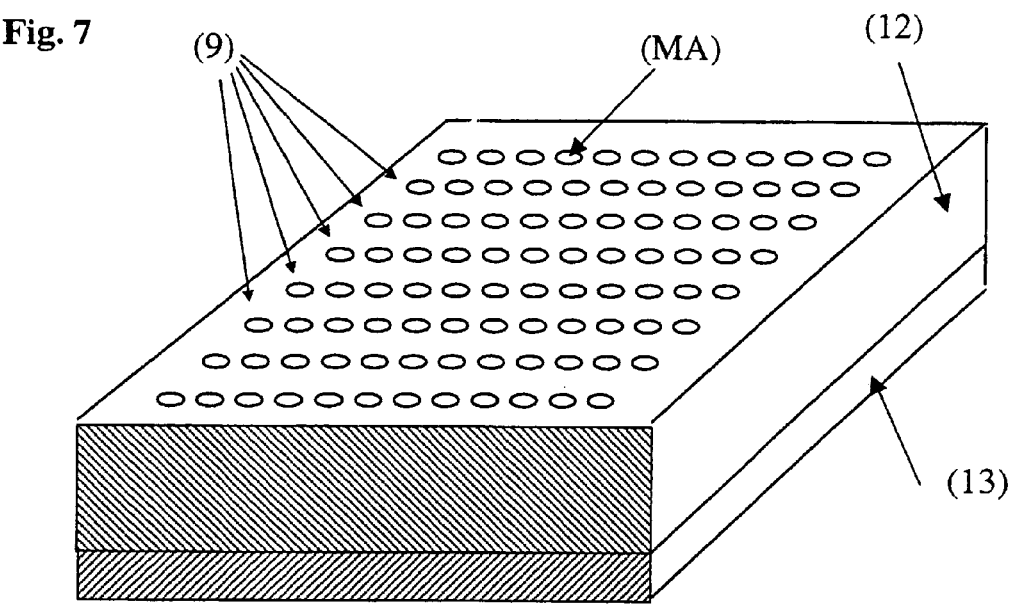
FIG. 7 is a schematic view of a rectangular array in accordance with the present invention.
Figure 8:
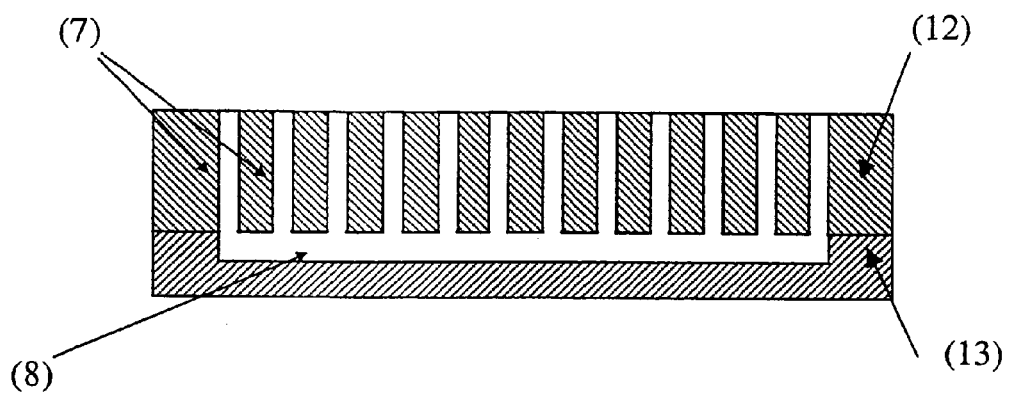
FIG. 8 is a sectional view of the array of FIG. 7.

In one embodiment of the invention, one or more of the reagents used are immobilised in the microarea (MA). This alternative configuration is illustrated in FIG. 4, where reagents (11) are immobilised on the rim (5) of a microchannel, allowing washing steps to be performed by overflowing the microchannel. Immobilisation may be achieved via covalent bonds, affinity bonds, physical adsorption etc. Typical affinity bonds are those formed by having strepavidin or a high affinity antibody bound to a solid support in the microarea (MA) and then binding a desired reagent conjugated with biotin or with the hapten against which the antibody is specific to the solid support bound strepavidin/high affinity antibody.

The method for replacing solvents can be used in a method to prevent samples from becoming desiccated. One example of a method for achieving this comprises the following steps:

providing a microarea for receiving a sample;

connecting the microarea (preferably via a microchannel) to a reservoir of solvent;

applying the sample to the microarea;

allowing solvent to evaporate from said microarea; and continuously replacing said evaporated solvent with solvent from said reservoir.

In this example, it is preferable that the diffusion rate of the sample in the solvent is less than the flow rate of solvent from the reservoir so that the sample does not diffuse away from the microarea.

A second example of a method for preventing samples becoming desiccated comprises the additional step of:

anchoring the sample to the microarea.

In this example, the flow rate of solvent from the reservoir may be less than the diffusion rate of the sample in the solvent once the sample is firmly attached to the microarea and is unable to diffuse away.

The sample can be applied to the microarea by dispensing from above, for example by dropping into the microarea a drop of solvent containing the sample, or from below, for example by injecting the sample into the microchannel between the reservoir and the microarea and allowing the flow of solvent to bring the sample to the micro area.

The microfluidic device according to the invention can suitably be fabricated in the form of a circular (FIGS. 5 and 6) or rectangular array format (FIGS. 7 and 8), although any other shape is also conceivable.

A circular format means that there are one or more microareas (chambers) that are placed radially and in different directions from a centre. The distance from the centre to individual microareas (chambers) may be equal or different. The reservoir is preferably in the centre. The microchannels may be radially directed from the centre and communicate with one or more microareas. The microchannels may also be in the form of a common, flat-like microchannel or reservoir beneath the microareas (chambers) and communicating upwardly via traditional microchannels.

In rectangular formats there are microareas (chambers) that form a rectangular pattern. The microchannel arrangement may be in analogy with the circular format.

Microfluidic devices in the form of rotatable discs are known in the art. WO 97/21090 discloses a microanalytical/microsynthetic system for biological and chemical analysis, comprising a rotatable microplatform, e.g. a disc, having inlet ports, microchannels, detection chambers (microareas) and outlet ports through which fluid may flow. Preferably, a circular array comprises a disc and a plurality of microchannels (see FIGS. 5 and 6), each microchannel being radially dispersed about the centre of the said rotatable disc. The rotatable disc is adapted for rotation about its axis. Such adaptation may take the form of a hole at the axis of one or both substrates which is capable of engaging a drive shaft. Other methods of rotating the disc include clamping the disc and contacting the perimeter with a moving surface, for example moving wheels, or placing the disc on a turntable and spinning the turntable. Preferably the disc comprises a solvent inlet port located towards the centre of the disc and connected to radially dispersed microchannels, each microchannel having a sample reservoir located at the microchannel orifice that is located outward from the centre of the disc.

The configuration of the microchannels in the rectangular or circular format may be chosen to allow for application of a chemical compound, or a suspension of cells, to the sample reservoir filled with fluid medium.

The microfluidic device may also comprise a separate microchannel system for transporting one or more of the reactants needed to the microareas.

Suitably the circular or rectangular array format is a one- or two-piece construction assembled together to provide a closed structure with openings at defined positions to allow loading of the device with liquids and removal of waste liquids. In the simplest form, see, for example, FIGS. 6-7, the disc or wafer is produced as two complementary parts (12), (13), one or each carrying channel structures which, when affixed together, form a series of interconnected structures within the body of a solid disc or wafer. The microchannels may be formed by micro-machining methods in which the channels and chambers are micro-machined into the surface of a disc or wafer, and a cover, for example a plastic film, is adhered to the surface so as to enclose the channels and chambers.

Suitable glass or polymeric materials can be additionally selectively modified by chemical or physical means to alter the surface properties to confer a desired property, e.g. compatibility with cell growth, cell attachment and the attachment of biomolecules by covalent or non-covalent means.

Based on knowledge at the priority date, the variant given in FIGS. 1 and 2 corresponds to the best mode in October 1998.

The invention claimed is:

1. A method for replacing a solvent evaporating from a microvolume of sample containing solvent and reactant which are to be reacted in an open microarea of a microfluidic device comprising the step of replacing evaporated solvent continuously via a microchannel that transports solvent to the microarea from a solvent reservoir, wherein the solvent is miscible with the sample and the microvolume of solvent comprises the reactant for performing a reaction within the microvolume of solvent on the microarea.

2. The method of claim 1, wherein the microarea, microchannel and reservoir are parts of the microfluidic device.

3. A method for replacing solvents for preventing samples from becoming desiccated comprising the following steps:

providing a microfluidic device having an open microarea for carrying a sample connected to a solvent reservoir by a microchannel;

providing the sample to the microarea which sample contains one or more reactants and a solvent that is miscible with the sample;

allowing the solvent to evaporate from said microarea; and continuously replacing said evaporated solvent with solvent from said reservoir.

4. The method of claim 3 further comprising the step of anchoring the sample to the microarea.

5. The method of claim 2, wherein the reservoir is positioned so as to create an overpressure in the solvent which is in equilibrium with the interfacial pressure difference across the curved surface of the droplet or said reservoir is connected to pump means that either facilitate replacement of solvent by pumping solvent or pressurizing the reservoir.

6. The method of claim 2, wherein the microfluidic device comprises a plurality of microchannels and open chambers forming an array in the circular or rectangular format.

7. The method of claim 2, wherein one or more of the reactants are soluble in the solvent or bound to a solid support in contact with the microvolume.

8. The method of claim 3, wherein the microarea, microchannel and reservoir are parts of the microfluidic device.

* * * * *

UNITED STATES PATENT AND TRADEMARK OFFICE
CERTIFICATE OF CORRECTION

Page 1 of 1

PATENT NO.         : 7,323,345 B1
APPLICATION NO.    : 09/830795
DATED              : January 29, 2008
INVENTOR(S)        : Martin Stjernstrom It is certified that error appears in the above-identified patent and that said Letters Patent is hereby corrected as shown below:

Title page, item (73), should read;

\*\* Assignee: Gyros Patent AB, Uppsala (SE) \*\*

Signed and Sealed this
Twenty-fourth Day of July, 2012

David J. Kappos
*Director of the United States Patent and Trademark Office*